US008309588B2

(12) United States Patent (10) Patent No.: US 8,309,588 B2
Diehl et al. (45) Date of Patent: Nov. 13, 2012

(54) SYNERGISTIC MICROBICIDAL COMPOSITIONS

(75) Inventors: Megan Ann Diehl, Line Lexington, PA (US); Dolores A. Shaw, Collegeville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 13/111,006

(22) Filed: May 19, 2011

(65) Prior Publication Data

US 2011/0224270 A1 Sep. 15, 2011

Related U.S. Application Data

(62) Division of application No. 12/316,786, filed on Dec. 16, 2008.

(51) Int. Cl.
*A61K 31/425* (2006.01)
*A61K 31/225* (2006.01)
*A61K 31/22* (2006.01)
*A61K 31/23* (2006.01)

(52) U.S. Cl. ........ 514/373; 514/552; 514/551; 514/546; 514/547

(58) Field of Classification Search .......... 514/373, 514/560, 77, 546, 547, 551, 552
See application file for complete search history.

(56) References Cited

U.S. PATENT DOCUMENTS

| 5,028,620 A | 7/1991 | Hsu |
| 5,322,834 A | 6/1994 | Hsu |
| 7,468,384 B2 | 12/2008 | Levy et al. |
| 2004/0014799 A1 | 1/2004 | Antoni-Zimmermann et al. |
| 2006/0106024 A1* | 5/2006 | Levy et al. ............ 514/250 |
| 2007/0027109 A1 | 2/2007 | Comper |
| 2007/0207105 A1 | 9/2007 | Winn |
| 2009/0023688 A1 | 1/2009 | Levy et al. |
| 2009/0023790 A1 | 1/2009 | Levy et al. |

FOREIGN PATENT DOCUMENTS

| JP | 2006273719 | 10/2006 |
| WO | 2007007080 | 1/2007 |

OTHER PUBLICATIONS

Gervajio "Fatty acids and derivatives from coconut oil," Bailey's Industrial oil and fat products. Sixth Edition, Edited by Fereidon Shahidi, 2005, John Wiley & Sons Inc. pp. 1-56.*

* cited by examiner

*Primary Examiner* — Shengjun Wang
(74) *Attorney, Agent, or Firm* — Tifani M. Edwards

(57) ABSTRACT

This invention relates to synergistic combinations of selected microbicides in combination with a second microbicide or formulation ingredient or raw material. The combinations have greater efficacy than would be expected from combinations of the individual components. The combinations include mixtures of (a) 5-Chloro-2-methyl-4-isothiazolin-3-one+2-Methyl-4-isothiazolin-3-one, (b) Methyl-4-isothiazolin-3-one, or (c) 1,2-Benzisothiazolin-3-one with one or more of a variety of other compounds.

1 Claim, No Drawings

SYNERGISTIC MICROBICIDAL COMPOSITIONS

This invention relates to synergistic combinations of selected microbicides with other microbicides, formulation ingredients, or raw materials that result in a composition with greater antimicrobial activity than would be expected from combinations of the individual components.

In some cases, commercial microbicides cannot provide effective control of certain microorganisms, even at high use concentrations, due to weak activity against certain types of microorganisms, e.g., those resistant to some microbicides, or due to aggressive environmental conditions. Combinations of different microbicides are sometimes used to provide overall control of microorganisms in a particular end use environment. For example, combinations of 2-methyl-4-isothiazolin-3-one and other biocides are disclosed in U.S. Pat. App. Pub. No. 2004/0014799; combinations of 1,2-benzisothiazolin-3-one and other biocides are disclosed in U.S. Pat. App. Publ No. 2006/0106024, and combinations of 5-chloro-2-methyl-4-isothiazolin-3-one plus 2-methyl-4-isothiazolin-3-one and other biocides are disclosed in U.S. Pat. No. 5,322,834. However, there is still a need for additional combinations of microbicides, or combinations of microbicides with formulation ingredients or raw materials, having enhanced activity against various strains of microorganisms to provide effective control of such microorganisms. In addition, there is still a need for combinations containing lower levels of individual microbicides for environmental and economic benefit. The problem addressed by this invention is to provide such additional combinations of microbicides or microbicides with formulation ingredients or raw materials.

A first embodiment of the present invention is directed to a composition comprising a synergistic mixture of:
(a) a mixture of 5-chloro-2-methyl-4-isothiazolin-3-one and 2-methyl-4-isothiazolin-3-one; and
(b) one or more compounds selected from the group consisting of caprylic acid, glycerol monolaurate, glyceryl mono dicaprylate, glyceryl caprate, propylene glycol caprylate, propylene glycol monolaurate, lauric arginate, myristamidopropyl PG-dimonium chloride phosphate, ethylhexylglycerin, and caprylyl glycol.

A second embodiment of the present invention is directed to a composition comprising a synergistic mixture of:
(a) 2-methyl-4-isothiazolin-3-one; and
(b) one or more compounds selected from the group consisting of caprylic acid, glycerol monolaurate, glyceryl mono dicaprylate, glyceryl caprate, propylene glycol caprylate, propylene glycol monolaurate, lauric arginate, myristamidopropyl PG-dimonium chloride phosphate, and ethylhexylglycerin.

A third embodiment of the present invention is directed to a composition comprising a synergistic mixture of:
(a) 1,2-benzisothiazolin-3-one; and
(b) one or more compounds selected from the group consisting of caprylic acid, glycerol monolaurate, glyceryl mono dicaprylate, glyceryl caprate, propylene glycol caprylate, propylene glycol monolaurate, lauric arginate, myristamidopropyl PG-dimonium chloride phosphate, and ethylhexylglycerin.

"CMIT" is 5-chloro-2-methyl-4-isothiazolin-3-one, also referred to by the name 5-chloro-2-methyl-3-isothiazolone or chloromethylisothiazolinone. "MIT" is 2-methyl-4-isothiazolin-3-one, also referred to by the name 2-methyl-3-isothiazolone or methylisothiazolinone. "BIT" is 1,2-benzisothiazolin-3-one. "Caprylic acid" is octanoic acid. "Glycerol monolaurate" is the mono ester of dodecanoic acid and glycerol, also known as glyceryl laurate. "Glyceryl mono dicaprylate" is the monoester of octanoic acid and glycerol, also known as glyceryl caprylate. "Propylene glycol caprylate" is the monoester of octanoic acid and 1,2-propanediol. "Propylene glycol monolaurate" is the monoester of dodecanoic acid and 1,2-propanediol. "Lauric arginate" is N-α-lauoryl-L-arginine ethyl ester monohydrochloride, also known as ethyl-N-α-dodecanoyl-L-arginate hydrochloride. "Myristamidopropyl PG-dimonium chloride phosphate is 1-propanaminium, 3,3',3"-[phosphinylidynetris(oxy)]-tris-[N-(aminopropyl)-2-hydroxy-N,N-dimethyl-N,N',N"-tri-$C_{6-18}$ acyl deriv. trichlorides. "Ethylhexylglycerin" is 3-[(2-ethylhexyl)oxy]-1,2propanediol. "Caprylyl glycol" is 1,2-octanediol.

As used herein, the following terms have the designated definitions, unless the context clearly indicates otherwise. The term "microbicide", "biocide", "preservative" or "antimicrobial" refers to a compound capable of killing, inhibiting the growth of, or controlling the growth of microorganisms at a locus; microbicides include bactericides, fungicides and algaecides. The term "microorganism" includes, for example, fungi (such as yeast and mold), bacteria, and algae. The term "locus" refers to an industrial system or product, a personal care system or product, or a home care system or product subject to contamination by microorganisms. The term "compound" refers to a microbicide, a formulation ingredient, or a raw material. The following abbreviations are used throughout this specification: ppm=parts per million by weight (weight/weight), mL=milliliter, ATCC=American Type Culture Collection, MBC=minimum biocidal concentration, and MIC=minimum inhibitory concentration. Unless otherwise specified, temperatures are in degrees centigrade (° C.), and references to percentages (%) are by weight. Amounts of organic microbicides are given on an active ingredient basis in ppm (w/w). Ratios are by weight and may be expressed as, for example, 1/400 or 1:400.

The compositions of the present invention unexpectedly have been found to provide enhanced microbicidal efficacy at an active ingredient level lower than what would be expected for a combination of the individual microbicides, or the microbicides in combination with formulation ingredients or raw materials, based on their individual efficacy.

In the first embodiment of this invention the ratio of CMIT to MIT is 5:1 or less (that is, five parts or less of CMIT to one part MIT). In another embodiment, the ratio of CMIT to MIT is 3:1 or less. In a further embodiment, the ratio of CMIT to MIT is 1:1 or less. In another embodiment of this invention, the ratio of CMIT to MIT is from 2.3:1 to 4:1, preferably 2.5:1 to 3.3:1.

In one embodiment of the invention, in which the composition contains halogenated 3-isothiazolones (other than CMIT in the first embodiment), the composition contains relatively low levels of halogenated 3-isothiazolones, preferably no more than 1000 ppm, more preferably no more than 500 ppm, more preferably no more than 100 ppm, and most preferably no more than 50 ppm. Concentrations of halogenated 3-isothiazolones in the compositions of this invention are based on the total weight of components a), b), and the halogenated 3-isothiazolones, exclusive of any amounts of solvents, carriers, dispersants, stabilizers or other materials which may be present. In one embodiment of the second and third embodiments of the invention, the antimicrobial composition contains no more than 1000 ppm of CMIT, preferably no more than 500 ppm, more preferably no more than 100 ppm, and most preferably no more than 50 ppm.

In one embodiment of the invention, the composition comprises a mixture of CMIT and MIT and caprylic acid. Preferably, a weight ratio of CMIT+MIT to caprylic acid is from 1/400 to 1/60,000.

In one embodiment of the invention, the composition comprises a mixture of CMIT and MIT and glycerol monolaurate. Preferably, a weight ratio of CMIT and MIT to glycerol monolaurate is from 1/40 to 1/8000.

In one embodiment of the invention, the composition comprises a mixture of CMIT and MIT and glyceryl mono dicaprylate. Preferably, a weight ratio of CMIT and MIT to glyceryl mono dicaprylate is from 1/400 to 1/8000.

In one embodiment of the invention, the composition comprises a mixture of CMIT and MIT and glyceryl caprate. Preferably, a weight ratio of CMIT and MIT to glyceryl caprate is from 1/100 to 1/800.

In one embodiment of the invention, the composition comprises a mixture of CMIT and MIT and propylene glycol caprylate. Preferably, a weight ratio of CMIT and MIT to propylene glycol caprylate is from 1/40 to 1/13,333.

In one embodiment of the invention, the composition comprises a mixture of CMIT and MIT and propylene glycol monolaurate. Preferably, a weight ratio of CMIT and MIT to propylene glycol monolaurate is from 1/2000 to 1/20,000.

In one embodiment of the invention, the composition comprises a mixture of CMIT and MIT and lauric arginate. Preferably, a weight ratio of CMIT and MIT to lauric arginate is from 1/50 to 1/8000.

In one embodiment of the invention, the composition comprises a mixture of CMIT and MIT and myristamidopropyl PG-dimonium chloride phosphate. Preferably, a weight ratio of CMIT and MIT to myristamidopropyl PG-dimonium chloride phosphate is from 1/20 to 1/8000.

In one embodiment of the invention, the composition comprises a mixture of CMIT and MIT and ethylhexylglycerin. Preferably, a weight ratio of CMIT and MIT to ethylhexylglycerin is from 1/200 to 1/20,000.

In one embodiment of the invention, the composition comprises a mixture of CMIT and MIT and caprylyl glycol. Preferably, a weight ratio of CMIT and MIT to caprylyl glycol is from 1/400 to 1/16,000.

In one embodiment of the invention, the composition comprises MIT and caprylic acid. Preferably, a weight ratio of MIT to caprylic acid is from 1/1.3 to 1/10.

In one embodiment of the invention, the composition comprises MIT and glycerol monolaurate. Preferably, a weight ratio of MIT to glycerol monolaurate is from 1/2 to 1/2.5.

In one embodiment of the invention, the composition comprises MIT and glyceryl mono dicaprylate. Preferably, a weight ratio of MIT to glyceryl mono dicaprylate is from 1/0.53 to 1/2.4.

In one embodiment of the invention, the composition comprises MIT and glyceryl caprate. Preferably, a weight ratio of MIT to glyceryl caprate is from 1/0.2 to 1/8.

In one embodiment of the invention, the composition comprises MIT and propylene glycol caprylate. Preferably, a weight ratio of MIT to propylene glycol caprylate is from 1/0.03 to 1/1000.

In one embodiment of the invention, the composition comprises MIT and propylene glycol monolaurate. Preferably, a weight ratio of MIT to propylene glycol monolaurate is from 1/4 to 1/20.

In one embodiment of the invention, the composition comprises MIT and lauric arginate. Preferably, a weight ratio of MIT to lauric arginate is from 1/0.03 to 1/24.

In one embodiment of the invention, the composition comprises MIT and myristamidopropyl PG-dimonium chloride phosphate. Preferably, a weight ratio of MIT to myristamidopropyl PG-dimonium chloride phosphate is from 1/0.01 to 1/32.

In one embodiment of the invention, the composition comprises MIT and ethylhexylglycerin. Preferably, a weight ratio of MIT to ethylhexylglycerin is from 1/0.6 to 1/400.

In one embodiment of the invention, the composition comprises BIT and caprylic acid. Preferably, a weight ratio of BIT to caprylic acid is from 1/8 to 1/2400.

In one embodiment of the invention, the composition comprises BIT and glycerol monolaurate. Preferably, a weight ratio of BIT to glycerol monolaurate is from 1/10 to 1/533.

In one embodiment of the invention, the composition comprises BIT and glyceryl mono dicaprylate. Preferably, a weight ratio of BIT to glyceryl mono dicaprylated is from 1/8 to 1/400.

In one embodiment of the invention, the composition comprises BIT and glyceryl caprate. Preferably, a weight ratio of BIT to glyceryl caprate is from 1/1 to 1/67.

In one embodiment of the invention, the composition comprises BIT and propylene glycol caprylate. Preferably, a weight ratio of BIT to propylene glycol caprylate is from 1/0.2 to 1/2000.

In one embodiment of the invention, the composition comprises BIT and propylene glycol monolaurate. Preferably, a weight ratio of BIT to propylene glycol monolaurate is from 1/300 to 1/3200.

In one embodiment of the invention, the composition comprises BIT and lauric arginate. Preferably, a weight ratio of BIT to lauric arginate is from 1/0.1 to 1/200.

In one embodiment of the invention, the composition comprises BIT and myristamidopropyl PG-dimonium chloride phosphate. Preferably, a weight ratio of BIT to myristamidopropyl PG-dimonium chloride phosphate is from 1/0.2 to 1/200.

In one embodiment of the invention, the composition comprises BIT and ethylhexylglycerin. Preferably, a weight ratio of BIT to ethylhexylglycerin is from 1/1.5 to 1/3200.

The microbicides, formulation ingredients, and raw materials in each composition of this invention may be used "as is" or may first be formulated with a solvent or a solid carrier. Suitable solvents include, for example, water; glycols, such as, for example, ethylene glycol, propylene glycol, diethylene glycol, dipropylene glycol, polyethylene glycol, and polypropylene glycol; glycol ethers; alcohols, such as, for example, methanol, ethanol, propanol, phenethyl alcohol and phenoxypropanol; ketones, such as, for example, acetone and methyl ethyl ketone; esters, such as, for example, ethyl acetate, butyl acetate, triacetyl citrate, and glycerol triacetate; carbonates, such as, for example, propylene carbonate and dimethyl carbonate; and mixtures thereof. It is preferred that the solvent is selected from water, glycols, glycol ethers, esters and mixtures thereof. Suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate), and charcoal.

When a microbicide, formulation ingredient, or raw material component is formulated in a solvent, the formulation may optionally contain surfactants. When such formulations contain surfactants, they are generally in the form of emulsion concentrates, emulsions, microemulsion concentrates, or microemulsions. Emulsion concentrates form emulsions upon the addition of a sufficient amount of water. Microemulsion concentrates form microemulsions upon the addition of a sufficient amount of water. Such emulsion and microemulsion concentrates are generally well known in the art; it is preferred that such formulations are free of surfactants. U.S. Pat. No. 5,444,078 may be consulted for further general and specific details on the preparation of various microemulsions and microemulsion concentrates.

A microbicide, formulation ingredient, or raw material component also may be formulated in the form of a dispersion. The solvent component of the dispersion may be an organic solvent or water, preferably water. Such dispersions may contain adjuvants such as, for example, co-solvents, thickeners, anti-freeze agents, dispersants, fillers, pigments, surfactants, biodispersants, sulfosuccinates, terpenes, furanones, polycations, stabilizers, scale inhibitors, and anti-corrosion additives.

When the microbicide, formulation ingredient, or raw material are each first formulated with a solvent, the solvent used for the first component may be the same as or different from the solvent used to formulate the other component. Water is the preferred for many biocide applications. It is preferred that the two solvents are miscible.

Those skilled in the art will recognize that the microbicide, formulation ingredient, or raw material components of the present invention may be added to a locus sequentially, simultaneously, or may be combined before being added to the locus. In one embodiment of the invention, the first component and the second component are added to a locus simultaneously or sequentially. When the components are added simultaneously or sequentially, each may independently contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, sulfosuccinates, terpenes, furanones, polycations, stabilizers, scale inhibitors and anti-corrosion additives.

The compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions onto, into, or at a locus subject to microbial attack. Suitable loci include, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; lattices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household and personal care products, such as, for example, bathroom and kitchen cleaners; cosmetics; lotions, moisturizers, toiletries; hair styling creams, pastes, or gums; conditioners, 2 in 1 conditioning shampoos, body wash/shower gels, liquid soaps, sunscreen lotions and sprays, tanning lotions, skin care lotions, one and two-part hair dyes, permanent waving formulations, soaps; detergents; cleaners; floor polishes; laundry rinse water; metalworking fluids; conveyor lubricants; hydraulic fluids; leather and leather products; textiles; textile products; wood and wood products, such as, for example, plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

In one embodiment, the compositions of the present invention are used to inhibit the growth of microorganisms at a locus selected from one or more of cosmetics; sunscreens, lotions, toiletries; hair styling creams, pastes, or gums; conditioners, 2 in 1 conditioning shampoos, body wash/shower gels, liquid soaps, sunscreen lotions and sprays, tanning lotions, skin care lotions, one and two-part hair dyes, permanent waving formulations, soaps; and detergents.

The specific amount of the composition of this invention necessary to inhibit or control the growth of microorganisms and higher aquatic life forms in a locus depends upon the particular locus to be protected. Typically, the amount of the composition of the present invention to control the growth of microorganisms in a locus is sufficient if it provides from 0.1 to 1,000 ppm of the 3-isothiazoline ingredient of the composition in the locus. It is preferred that the 3-isothiazolone ingredients of the composition be present in the locus in an amount of at least 0.5 ppm, more preferably at least 1 ppm and most preferably at least 10 ppm. It is preferred that the isothiazolone ingredients of the composition be present in the locus in an amount of no more than 1000 ppm, more preferably no more than 500 ppm, and most preferably no more than 200 ppm.

The compositions of this invention may optionally contain one or more additional microbicides in order to afford a composition having broader efficacy against microorganisms. Such microbicides are selected from known microbicides on the basis of their ability to control specific microorganisms and the specific locus to be preserved.

EXAMPLES

Materials and Methods

The synergism of the combination of the present invention was demonstrated by testing a wide range of concentrations and ratios of the compounds.

One measure of synergism is the industrially accepted method described by Kull, F. C.; Eisman, P. C.; Sylwestrowicz, H. D. and Mayer, R. L., in *Applied Microbiology* 9:538-541 (1961), using the ratio determined by the formula:

$$Q_a/Q_A + Q_b/Q_B = \text{Synergy Index("SI")}$$

wherein:
$Q_A$=concentration of compound A (first component) in ppm, acting alone, which produced an end point (MIC of Compound A).
$Q_a$=concentration of compound A in ppm, in the mixture, which produced an end point.
$Q_B$=concentration of compound B (second component) in ppm, acting alone, which produced an end point (MIC of Compound B).
$Q_b$=concentration of compound B in ppm, in the mixture, which produced an end point.

When the sum of $Q_a/Q_A$ and $Q_b/Q_B$ is greater than one, antagonism is indicated. When the sum is equal to one, additivity is indicated, and when less than one, synergy is demonstrated. The lower the SI, the greater is the synergy shown by that particular mixture. The minimum inhibitory concentration (MIC) of a microbicide is the lowest concentration tested under a specific set of conditions that prevents the growth of the tested microorganisms.

Synergy tests were conducted using standard microtiter plate assays with media designed for optimal growth of the test microorganism. Minimal salt medium supplemented with 0.2% glucose and 0.1% yeast extract (M9GY medium) was used for testing bacteria; Potato Dextrose Broth (PDB medium) was used for testing yeast and mold. In this method, a wide range of combinations of microbicides and other personal care raw materials was tested by conducting high resolution MIC assays in the presence of various concentrations of CMIT/MIT, MIT, or BIT. High resolution MICs were determined by adding varying amounts of microbicide to one column of a microtitre plate and doing subsequent ten-fold dilutions using an automated liquid handling system to obtain a series of endpoints ranging from 2 ppm to 10,000 ppm active ingredient.

The synergy of the combinations of the present invention was determined against a bacterium, *Escherichia coli* (*E. coli*—ATCC #8739), a yeast, *Candida albicans* (*C. albicans*—ATCC 10231), and a mold, *Aspergillus niger* (*A. niger*—ATCC 16404). The bacteria were used at a concentration of about $5 \times 10^6$ bacteria per mL and the yeast and mold at $5 \times 10^5$ fungi per mL. These microorganisms are representative of natural contaminants in many consumer and industrial applications. The plates were visually evaluated for microbial growth (turbidity) to determine the MIC after various incubation times at 25° C. (yeast and mold) or 30° C. (bacteria).

The test results for demonstration of synergy of the CMIT/MIT combinations of the present invention are shown below in Tables 1 through 10. In each test, First Component (A) was CMIT/MIT and the Second Component (B) was the other microbicide or personal care ingredient. Each table shows the specific combinations of CMIT/MIT and the second component; results against the microorganisms tested with incubation times; the end-point activity in ppm measured by the MIC for CMIT/MIT alone ($Q_A$), for the second component alone ($Q_B$), for CMIT/MIT in the mixture ($Q_a$) and for second component in the mixture ($Q_b$); the calculated SI value; and the range of synergistic ratios for each combination tested (CMIT/MIT/second component or A/B).

The test results for demonstration of synergy of the MIT combinations of the present invention are shown below in Tables 11 through 19. In each test, First Component (A) was MIT and the Second Component (B) was the other microbicide or personal care ingredient. Each table shows the specific combinations of MIT and the second component; results against the microorganisms tested with incubation times; the end-point activity in ppm measured by the MIC for MIT alone ($Q_A$), for the second component alone ($Q_B$), for MIT in the mixture ($Q_a$) and for second component in the mixture ($Q_b$); the calculated SI value; and the range of synergistic ratios for each combination tested (MIT/second component or A/B).

The test results for demonstration of synergy of the BIT combinations of the present invention are shown below in Tables 20 through 28. In each test, First Component (A) was BIT and the Second Component (B) was the other microbicide or personal care ingredient. Each table shows the specific combinations of BIT and the second component; results against the microorganisms tested with incubation times; the end-point activity in ppm measured by the MIC for BIT alone ($Q_A$), for the second component alone ($Q_B$), for BIT in the mixture ($Q_a$) and for second component in the mixture ($Q_b$); the calculated SI value; and the range of synergistic ratios for each combination tested (BIT/second component or A/B).

In each of the comparisons, the effective synergistic ratio may vary among the microorganisms tested and the various combinations of components A and B. Data in the tables below include the range of ratios that were found to be synergistic. Not all data which were collected outside of the synergistic ranges are reported.

TABLE 1

First Component (A) = Chloromethylisothiazolinone/methylisothiazolinone (CMIT/MIT)
Second Component (B) = Caprylic acid

| Microorganism | $Q_a$ | $Q_b$ | SI | A/B |
|---|---|---|---|---|
| *E. coli* 8739 - M9GY | 0 | 8000 | 1.00 | — |
| (2 days) | 0.1 | 6000 | 0.80 | 1/60,000 |
| | 0.4 | 5000 | 0.83 | 1/12,500 |
| | 0.4 | 6000 | 0.95 | 1/15,000 |
| | 0.5 | 5000 | 0.88 | 1/10,000 |
| | 0.75 | 3000 | 0.75 | 1/4,000 |
| | 0.75 | 4000 | 0.88 | 1/5,333 |
| | 1 | 2000 | 0.75 | 1/2,000 |
| | 1 | 3000 | 0.88 | 1/3,000 |
| | 2 | 0 | 1.00 | — |
| *C. albicans* 10231 - PDB | 0 | 2000 | 1.00 | — |
| (6 days) | 0.2 | 2000 | 1.10 | 1/10,000 |
| | 0.5 | 2000 | 1.25 | 1/4,000 |
| | 1 | 2000 | 1.50 | 1/2,000 |
| | 2 | 0 | 1.00 | — |
| *A. niger* 16404 - PDB | 0 | 2000 | 1.00 | — |
| (3 days) | 1 | 400 | 0.70 | 1/400 |
| | 1 | 500 | 0.75 | 1/500 |
| | 1 | 600 | 0.80 | 1/600 |
| | 1 | 800 | 0.90 | 1/800 |
| | 1 | 1000 | 1.00 | 1/1,000 |
| | 2 | 0 | 1.00 | — |

The ratios of CMIT and MIT to caprylic acid tested ranged from 1/10 to 1/100,000. The synergistic ratios of CMIT and MIT to caprylic acid range from 1/400 to 1/60,000. The CMIT and MIT and caprylic acid combinations show enhanced control of bacteria and mold.

TABLE 2

First Component (A) = Chloromethylisothiazolinone/methylisothiazolinone (CMIT/MIT)
Second Component (B) = Glycerol monolaurate

| Microorganism | $Q_a$ | $Q_b$ | SI | A/B |
|---|---|---|---|---|
| *E. coli* 8739 - M9GY | 0 | 20000 | 1.00 | — |
| (1 day) | 0.2 | 20000 | 1.10 | 1/100,000 |
| | 0.4 | 20000 | 1.20 | 1/50,000 |
| | 2.00 | 0 | 1.00 | — |
| *C. albicans* 10231 - PDB | 0 | 20000 | 1.00 | — |
| (1 day) | 0.2 | 20000 | 1.10 | 1/100,000 |
| | 0.4 | 20000 | 1.20 | 1/50,000 |
| | 2.00 | 0 | 1.00 | — |
| *A. niger* 16404 - PDB | 0 | 20000 | 1.00 | — |
| (3 days) | 0.25 | 20000 | 1.13 | 1/80,000 |
| | 0.75 | 20000 | 1.38 | 1/26,666 |
| | 1 | 40 | 0.50 | 1/40 |
| | 1 | 50 | 0.50 | 1/50 |
| | 1 | 60 | 0.50 | 1/60 |
| | 1 | 80 | 0.50 | 1/80 |
| | 1 | 100 | 0.51 | 1/100 |
| | 1 | 200 | 0.51 | 1/200 |
| | 1 | 300 | 0.52 | 1/300 |
| | 1 | 400 | 0.52 | 1/400 |
| | 1 | 500 | 0.53 | 1/500 |
| | 1 | 600 | 0.53 | 1/600 |
| | 1 | 800 | 0.54 | 1/800 |
| | 1 | 1000 | 0.55 | 1/1,000 |
| | 1 | 2000 | 0.60 | 1/2,000 |
| | 1 | 3000 | 0.65 | 1/3,000 |
| | 1 | 4000 | 0.70 | 1/4,000 |
| | 1 | 5000 | 0.75 | 1/5,000 |
| | 1 | 6000 | 0.80 | 1/6,000 |
| | 1 | 8000 | 0.90 | 1/8,000 |
| | 1 | 10000 | 1.00 | 1/10,000 |
| | 2.00 | 0 | 1.00 | — |

The ratios of CMIT and MIT to glycerol monolaurate tested ranged from 1/10 to 1/100,000. The synergistic ratios of CMIT and MIT to glycerol monolaurate range from 1/40 to 1/8,000. The CMIT and MIT and glycerol monolaurate combinations show enhanced control of mold.

TABLE 3

First Component (A) = Chloromethylisothiazolinone/methylisothiazolinone (CMIT/MIT)
Second Component (B) = Glyceryl mono dicaprylate

| Microorganism | $Q_a$ | $Q_b$ | SI | A/B |
|---|---|---|---|---|
| E. coli 8739 - M9GY | 0 | 3000 | 1.00 | — |
| (2 days) | 0.4 | 2000 | 0.87 | 1/5,000 |
| | 0.5 | 2000 | 0.92 | 1/4,000 |
| | 1 | 800 | 0.77 | 1/800 |
| | 1 | 1000 | 0.83 | 1/1,000 |
| | 2.00 | 0 | 1.00 | — |
| C. albicans 10231 - PDB | 0 | 80 | 1.00 | — |
| (1 day) | 0.2 | 80 | 1.10 | 1/400 |
| | 0.4 | 100 | 1.45 | 1/250 |
| | 2.00 | 0 | 1.00 | — |
| A. niger 16404 - PDB | 0 | 2000 | 1.00 | — |
| (3 days) | 0.125 | 1000 | 0.56 | 1/8,000 |
| | 0.25 | 1000 | 0.63 | 1/4,000 |
| | 0.5 | 800 | 0.65 | 1/1,600 |
| | 0.5 | 1000 | 0.75 | 1/2,000 |
| | 0.75 | 800 | 0.78 | 1/1,067 |
| | 0.75 | 1000 | 0.88 | 1/1,333 |
| | 1 | 400 | 0.70 | 1/400 |
| | 1 | 500 | 0.75 | 1/500 |
| | 1 | 600 | 0.80 | 1/600 |
| | 1 | 800 | 0.90 | 1/800 |
| | 1 | 1000 | 1.00 | 1/1,000 |
| | 2 | 0 | 1.00 | — |

The ratios of CMIT and MIT to glyceryl mono dicaprylate tested ranged from 1/1 to 1/100,000. The synergistic ratios of CMIT and MIT to glyceryl mono dicaprylate range from 1/400 to 1/8,000. The CMIT and MIT and glyceryl mono dicaprylate combinations show enhanced control of bacteria and mold.

TABLE 4

First Component (A) = Chloromethylisothiazolinone/methylisothiazolinone (CMIT/MIT)
Second Component (B) = Glyceryl caprate

| Microorganism | $Q_a$ | $Q_b$ | SI | A/B |
|---|---|---|---|---|
| E. coli 8739 - M9GY | 0 | 20000 | 1.00 | — |
| (1 day) | 0.2 | 20000 | 1.10 | 1/100,000 |
| | 0.4 | 20000 | 1.20 | 1/50,000 |
| | 0.75 | 20000 | 1.38 | 1/27,000 |
| | 1 | 20000 | 1.50 | 1/20,000 |
| | 2.00 | 0 | 1.00 | — |
| C. albicans 10231 - PDB | 0 | 2000 | 1.00 | — |
| (1 day) | 0.2 | 2000 | 1.10 | 1/10,000 |
| | 0.5 | 2000 | 1.25 | 1/4,000 |
| | 1 | 2000 | 1.50 | 1/2,000 |
| | 2.00 | 0 | 1.00 | — |
| A. niger 16404 - PDB | 0 | 2000 | 1.00 | — |
| (3 days) | 0.125 | 2000 | 1.06 | 1/16,000 |
| | 0.5 | 2000 | 1.25 | 1/4,000 |
| | 1 | 100 | 0.55 | 1/100 |
| | 1 | 200 | 0.60 | 1/200 |
| | 1 | 300 | 0.65 | 1/300 |
| | 1 | 400 | 0.70 | 1/400 |
| | 1 | 500 | 0.75 | 1/500 |
| | 1 | 600 | 0.80 | 1/600 |
| | 1 | 800 | 0.90 | 1/800 |
| | 2 | 0 | 1.00 | — |

The ratios of CMIT and MIT to glyceryl caprate tested ranged from 1/10 to 1/100,000. The synergistic ratios of CMIT and MIT to glyceryl caprate range from 1/100 to 1/800. The CMIT and MIT and glyceryl caprate combinations show enhanced control of mold.

TABLE 5

First Component (A) = Chloromethylisothiazolinone/methylisothiazolinone (CMIT/MIT)
Second Component (B) = Propylene glycol caprylate

| Microorganism | $Q_a$ | $Q_b$ | SI | A/B |
|---|---|---|---|---|
| E. coli 8739 - M9GY | 0 | 20000 | 1.00 | — |
| (1 day) | 0.4 | 20000 | 1.20 | 1/50,000 |
| | 0.75 | 3000 | 0.53 | 1/4,000 |
| | 0.75 | 4000 | 0.58 | 1/5,333 |
| | 0.75 | 5000 | 0.63 | 16,667 |
| | 0.75 | 6000 | 0.68 | 1/8.000 |
| | 0.75 | 8000 | 0.78 | 1/10,667 |
| | 0.75 | 10000 | 0.88 | 1/13,333 |
| | 1 | 2000 | 0.60 | 1/2,000 |
| | 1 | 3000 | 0.65 | 1/3,000 |
| | 1 | 4000 | 0.70 | 1/4,000 |
| | 1 | 5000 | 0.75 | 1/5,000 |
| | 1 | 6000 | 0.80 | 1/6,000 |
| | 1 | 8000 | 0.90 | 1/8,000 |
| | 2.00 | 0 | 1.00 | — |
| C. albicans 10231 - PDB | 0 | 100 | 1.00 | — |
| (1 day) | 0.1 | 60 | 0.65 | 1/600 |
| | 0.1 | 80 | 0.85 | 1/800 |
| | 0.2 | 50 | 0.60 | 1/250 |
| | 0.2 | 60 | 0.70 | 1/300 |
| | 0.2 | 80 | 0.90 | 1/400 |
| | 0.4 | 50 | 0.70 | 1/125 |
| | 0.4 | 60 | 0.80 | 1/150 |
| | 0.5 | 50 | 0.75 | 1/100 |
| | 0.5 | 60 | 0.85 | 1/120 |
| | 0.75 | 30 | 0.68 | 1/40 |
| | 0.75 | 40 | 0.78 | 1/53 |
| | 0.75 | 50 | 0.88 | 1/67 |
| | 0.75 | 60 | 0.98 | 1/80 |
| | 2.00 | 0 | 1.00 | — |
| A. niger 16404 - PDB | 0 | 2000 | 1.00 | — |
| (3 days) | 0.25 | 800 | 0.53 | 1/3,200 |
| | 0.25 | 1000 | 0.63 | 1/4,000 |
| | 0.5 | 1000 | 0.75 | 1/2,000 |
| | 0.75 | 500 | 0.63 | 1/667 |
| | 0.75 | 600 | 0.68 | 1/800 |
| | 0.75 | 800 | 0.78 | 1/1,067 |
| | 0.75 | 1000 | 0.88 | 1/1,333 |
| | 1 | 50 | 0.53 | 1/50 |
| | 1 | 60 | 0.53 | 1/60 |
| | 1 | 80 | 0.54 | 1/80 |
| | 1 | 100 | 0.55 | 1/100 |
| | 1 | 200 | 0.60 | 1/200 |
| | 1 | 300 | 0.65 | 1/300 |
| | 1 | 400 | 0.70 | 1/400 |
| | 1 | 500 | 0.75 | 1/500 |
| | 1 | 600 | 0.80 | 1/600 |
| | 1 | 800 | 0.90 | 1/800 |
| | 2 | 0 | 1.00 | — |

The ratios of CMIT and MIT to propylene glycol caprylate tested ranged from 1/1 to 1/100,000. The synergistic ratios of CMIT and MIT to propylene glycol caprylate range from 1/40 to 1/13,333. The CMIT and MIT and propylene glycol caprylate combinations show enhanced control of bacteria, yeast, and mold.

TABLE 6

First Component (A) = Chloromethylisothiazolinone/methylisothiazolinone (CMIT/MIT)
Second Component (B) = Propylene glycol monolaurate

| Microorganism | $Q_a$ | $Q_b$ | SI | A/B |
|---|---|---|---|---|
| E. coli 8739 - M9GY | 0 | 20000 | 1.00 | — |
| (1 day) | 0.2 | 20000 | 1.10 | 1/100000 |
| | 0.4 | 20000 | 1.20 | 1/50,000 |
| | 0.75 | 20000 | 1.38 | 1/26,667 |
| | 1 | 20000 | 1.50 | 1/20,000 |
| | 2.00 | 0 | 1.00 | — |

TABLE 6-continued

First Component (A) = Chloromethylisothiazolinone/
methylisothiazolinone (CMIT/MIT)
Second Component (B) = Propylene glycol monolaurate

| Microorganism | $Q_a$ | $Q_b$ | SI | A/B |
|---|---|---|---|---|
| C. albicans 10231 - PDB (1 day) | 0 | 20000 | 1.00 | — |
| | 0.4 | 20000 | 1.20 | 1/50,000 |
| | 0.5 | 10000 | 0.75 | 1/20,000 |
| | 0.75 | 10000 | 0.88 | 1/13,333 |
| | 1 | 3000 | 0.65 | 1/3,000 |
| | 1 | 4000 | 0.70 | 1/4,000 |
| | 1 | 5000 | 0.75 | 1/5,000 |
| | 1 | 6000 | 0.80 | 1/6,000 |
| | 1 | 8000 | 0.90 | 1/8,000 |
| | 2.00 | 0 | 1.00 | — |
| A. niger 16404 - PDB (3 days) | 0 | 20000 | 1.00 | — |
| | 0.5 | 20000 | 1.25 | 1/40,000 |
| | 1 | 2000 | 0.60 | 1/2,000 |
| | 1 | 3000 | 0.65 | 1/3,000 |
| | 1 | 4000 | 0.70 | 1/4,000 |
| | 1 | 5000 | 0.75 | 1/5,000 |
| | 1 | 6000 | 0.80 | 1/6,000 |
| | 1 | 8000 | 0.90 | 1/8,000 |
| | 2 | 0 | 1.00 | — |

The ratios of CMIT and MIT to propylene glycol monolaurate tested ranged from 1/10 to 1/100,000. The synergistic ratios of CMIT and MIT to propylene glycol monolaurate range from 1/2,000 to 1/20,000. The CMIT and MIT and propylene glycol monolaurate combinations show enhanced control of yeast and mold.

TABLE 7

First Component (A) = Chloromethylisothiazolinone/
methylisothiazolinone (CMIT/MIT)
Second Component (B) = Lauric arginate

| Microorganism | $Q_a$ | $Q_b$ | SI | A/B |
|---|---|---|---|---|
| E. coli 8739 - M9GY (1 day) | 0 | 200 | 1.00 | — |
| | 0.2 | 300 | 1.60 | 1/1,500 |
| | 0.5 | 200 | 1.25 | 1/400 |
| | 0.75 | 200 | 1.38 | 1/267 |
| | 1 | 200 | 1.50 | 1/200 |
| | 2.00 | 0 | 1.00 | — |
| C. albicans 10231 - PDB (1 day) | 0 | 800 | 1.00 | — |
| | 0.1 | 600 | 0.80 | 1/6,000 |
| | 0.2 | 500 | 0.73 | 1/2,500 |
| | 0.2 | 600 | 0.85 | 1/3,000 |
| | 0.4 | 300 | 0.58 | 1/750 |
| | 0.4 | 400 | 0.70 | 1/1,000 |
| | 0.4 | 500 | 0.83 | 1/1,250 |
| | 0.4 | 600 | 0.95 | 1/1,500 |
| | 0.5 | 300 | 0.63 | 1/600 |
| | 0.5 | 400 | 0.75 | 1/800 |
| | 0.5 | 500 | 0.88 | 1/1,000 |
| | 0.75 | 100 | 0.50 | 1/133 |
| | 0.75 | 200 | 0.63 | 1/267 |
| | 0.75 | 300 | 0.75 | 1/400 |
| | 0.75 | 400 | 0.88 | 1/533 |
| | 1 | 50 | 0.56 | 1/50 |
| | 1 | 60 | 0.58 | 1/60 |
| | 1 | 80 | 0.60 | 1/80 |
| | 1 | 100 | 0.63 | 1/100 |
| | 1 | 200 | 0.75 | 1/200 |
| | 1 | 300 | 0.88 | 1/300 |
| | 2.00 | 0 | 1.00 | — |
| A. niger 16404 - PDB (4 days) | 0 | 2000 | 1.00 | — |
| | 0.125 | 1000 | 0.56 | 1/8,000 |
| | 0.25 | 800 | 0.53 | 1/3,200 |
| | 0.25 | 1000 | 0.63 | 1/4,000 |
| | 0.5 | 1000 | 0.75 | 1/2,000 |
| | 0.75 | 800 | 0.78 | 1/1,067 |
| | 0.75 | 1000 | 0.88 | 1/1,333 |
| | 1 | 80 | 0.54 | 1/80 |

TABLE 7-continued

First Component (A) = Chloromethylisothiazolinone/
methylisothiazolinone (CMIT/MIT)
Second Component (B) = Lauric arginate

| Microorganism | $Q_a$ | $Q_b$ | SI | A/B |
|---|---|---|---|---|
| | 1 | 100 | 0.55 | 1/100 |
| | 1 | 200 | 0.60 | 1/200 |
| | 1 | 300 | 0.65 | 1/300 |
| | 1 | 400 | 0.70 | 1/400 |
| | 1 | 500 | 0.75 | 1/500 |
| | 1 | 600 | 0.80 | 1/600 |
| | 1 | 800 | 0.90 | 1/800 |
| | 2 | 0 | 1.00 | — |

The ratios of CMIT and MIT to lauric arginate tested ranged from 1/1 to 1/10,000. The synergistic ratios of CMIT and MIT to lauric arginate range from 1/50 to 1/8,000. The CMIT and MIT and lauric arginate combinations show enhanced control of yeast and mold.

TABLE 8

First Component (A) = Chloromethylisothiazolinone/
methylisothiazolinone (CMIT/MIT)
Second Component (B) = Myristamidopropyl PG-dimonium chloride phosphate

| Microorganism | $Q_a$ | $Q_b$ | SI | A/B |
|---|---|---|---|---|
| E. coli 8739 - M9GY (2 days) | 0 | 100 | 1.00 | — |
| | 0.1 | 80 | 0.85 | 1/800 |
| | 0.2 | 80 | 0.90 | 1/400 |
| | 0.75 | 80 | 1.18 | 1/107 |
| | 1 | 50 | 1.00 | 1/50 |
| | 2.00 | 0 | 1.00 | — |
| C. albicans 10231 - PDB (1 day) | 0 | 800 | 1.00 | — |
| | 0.4 | 600 | 0.95 | 1/1,500 |
| | 0.5 | 500 | 0.88 | 1/1,000 |
| | 0.5 | 600 | 1.00 | 1/1,200 |
| | 0.75 | 200 | 0.63 | 1/267 |
| | 0.75 | 300 | 0.75 | 1/400 |
| | 0.75 | 400 | 0.88 | 1/533 |
| | 1 | 20 | 0.53 | 1/20 |
| | 1 | 30 | 0.54 | 1/30 |
| | 1 | 40 | 0.55 | 1/40 |
| | 1 | 50 | 0.56 | 1/50 |
| | 1 | 60 | 0.58 | 1/60 |
| | 1 | 80 | 0.60 | 1/80 |
| | 1 | 100 | 0.63 | 1/100 |
| | 1 | 200 | 0.75 | 1/200 |
| | 1 | 300 | 0.88 | 1/300 |
| | 2.00 | 0 | 1.00 | — |
| A. niger 16404 - PDB (3 days) | 0 | 2000 | 1.00 | — |
| | 0.125 | 1000 | 0.56 | 1/8,000 |
| | 0.25 | 1000 | 0.63 | 1/4,000 |
| | 0.5 | 600 | 0.55 | 1/1,200 |
| | 0.5 | 800 | 0.65 | 1/1,600 |
| | 0.5 | 1000 | 0.75 | 1/2,000 |
| | 0.75 | 200 | 0.48 | 1/267 |
| | 0.75 | 300 | 0.53 | 1/400 |
| | 0.75 | 400 | 0.58 | 1/533 |
| | 0.75 | 500 | 0.63 | 1/667 |
| | 0.75 | 600 | 0.68 | 1/800 |
| | 0.75 | 800 | 0.78 | 1/1,067 |
| | 0.75 | 1000 | 0.88 | 1/1,333 |
| | 1 | 100 | 0.55 | 1/100 |
| | 1 | 200 | 0.60 | 1/200 |
| | 1 | 300 | 0.65 | 1/300 |
| | 1 | 400 | 0.70 | 1/400 |
| | 1 | 500 | 0.75 | 1/500 |
| | 1 | 600 | 0.80 | 1/600 |
| | 1 | 800 | 0.90 | 1/800 |
| | 2 | 0 | 1.00 | — |

The ratios of CMIT and MIT to myristamidopropyl PG-dimonium chloride phosphate tested ranged from 1/0.1 to 1/10,000. The synergistic ratios of CMIT and MIT to myristamidopropyl PG-dimonium chloride phosphate range from 1/20 to 1/8,000. The CMIT and MIT and myristamidopropyl PG-dimonium chloride phosphate combinations show enhanced control of bacteria, yeast and mold.

TABLE 9

First Component (A) = Chloromethylisothiazolinone/methylisothiazolinone (CMIT/MIT)
Second Component (B) = Ethylhexylglycerin

| Microorganism | $Q_a$ | $Q_b$ | SI | A/B |
|---|---|---|---|---|
| E. coli 8739 - M9GY (1 day) | 0 | 3000 | 1.00 | — |
| | 0.1 | 2000 | 0.72 | 1/20,000 |
| | 0.2 | 2000 | 0.77 | 1/10,000 |
| | 0.4 | 2000 | 0.87 | 1/5,000 |
| | 0.4 | 2000 | 0.87 | 1/5,000 |
| | 0.5 | 2000 | 0.92 | 1/4,000 |
| | 2.00 | 0 | 1.00 | — |
| C. albicans 10231 - PDB (1 day) | 0 | 2000 | 1.00 | — |
| | 0.2 | 2000 | 1.10 | 1/10,0000 |
| | 0.5 | 2000 | 1.25 | 1/4,000 |
| | 0.75 | 1000 | 0.88 | 1/1,333 |
| | 1 | 200 | 0.60 | 1/200 |
| | 1 | 300 | 0.65 | 1/300 |
| | 1 | 400 | 0.70 | 1/400 |
| | 1 | 500 | 0.75 | 1/500 |
| | 1 | 600 | 0.80 | 1/600 |
| | 1 | 800 | 0.90 | 1/800 |
| | 2.00 | 0 | 1.00 | — |
| A. niger 16404 - PDB (3 days) | 0 | 2000 | 1.00 | — |
| | 0.25 | 2000 | 1.13 | 1/8,000 |
| | 0.75 | 2000 | 1.38 | 1/2,667 |
| | 1 | 600 | 0.80 | 1/600 |
| | 1 | 800 | 0.90 | 1/800 |
| | 2 | 0 | 1.00 | — |

The ratios of CMIT and MIT to ethylhexylglycerin tested ranged from 1/10 to 1/100,000. The synergistic ratios of CMIT and MIT to ethylhexylglycerin range from 1/200 to 1/20,000. The CMIT and MIT and ethylhexylglycerin combinations show enhanced control of bacteria, yeast, and mold.

TABLE 10

First Component (A) = Chloromethylisothiazolinone/methylisothiazolinone (CMIT/MIT)
Second Component (B) = Caprylyl glycol

| Microorganism | $Q_a$ | $Q_b$ | SI | A/B |
|---|---|---|---|---|
| E. coli 8739 - M9GY (2 days) | 0 | 2000 | 1.00 | — |
| | 0.4 | 2000 | 1.20 | 1/5,000 |
| | 0.5 | 2000 | 1.25 | 1/4,000 |
| | 0.75 | 2000 | 1.38 | 1/2,667 |
| | 1 | 2000 | 1.50 | 1/2,000 |
| | 2.00 | 0 | 1.00 | — |
| C. albicans 10231 - PDB (1 day) | 0 | 3000 | 1.00 | — |
| | 0.2 | 3000 | 1.10 | 1/15,000 |
| | 0.4 | 2000 | 0.87 | 1/5,000 |
| | 0.4 | 2000 | 0.87 | 1/5,000 |
| | 0.5 | 2000 | 0.92 | 1/4,000 |
| | 1 | 2000 | 1.17 | 1/2,000 |
| | 2.00 | 0 | 1.00 | — |
| A. niger 16404 - PDB (3 days) | 0 | 3000 | 1.00 | — |
| | 0.125 | 2000 | 0.73 | 1/16,000 |
| | 0.25 | 2000 | 0.79 | 1/8,000 |
| | 0.5 | 2000 | 0.92 | 1/4,000 |
| | 0.75 | 1000 | 0.71 | 1/1,333 |
| | 1 | 400 | 0.63 | 1/400 |
| | 1 | 500 | 0.67 | 1/500 |
| | 1 | 600 | 0.70 | 1/600 |
| | 1 | 800 | 0.77 | 1/800 |
| | 1 | 1000 | 0.83 | 1/1,000 |
| | 2 | 0 | 1.00 | — |

The ratios of CMIT and MIT to caprylyl glycol tested ranged from 1/10 to 1/100,000. The synergistic ratios of CMIT and MIT to caprylyl glycol range from 1/400 to 1/16,000. The CMIT and MIT and caprylyl glycol combinations show enhanced control of yeast and mold.

TABLE 11

First Component (A) = Methylisothiazolinone (MIT)
Second Component (B) = Caprylic acid

| Microorganism | $Q_a$ | $Q_b$ | SI | A/B |
|---|---|---|---|---|
| E. coli 8739 - M9GY (1 day) | 0 | 8000 | 1.00 | — |
| | 5 | 8000 | 1.17 | 1/1,600 |
| | 10 | 5000 | 0.96 | 1/500 |
| | 20 | 3000 | 1.04 | 1/150 |
| | 30 | 0 | 1.00 | — |
| | Qa | Qb | | |
| C. albicans 10231 - PDB (6 days) | 0 | 2000 | 1.00 | — |
| | 25 | 2000 | 1.13 | 1/80 |
| | 50 | 2000 | 1.25 | 1/40 |
| | 75 | 2000 | 1.38 | 1/27 |
| | 150 | 2000 | 1.75 | 1/13 |
| | 200 | 0 | 1.00 | — |
| | $Q_a$ | $Q_b$ | | |
| A. niger 16404 - PDB (10 days) | 0 | 2000 | 1.00 | — |
| | 100 | 600 | 0.50 | 1/6 |
| | 100 | 800 | 0.60 | 1/8 |
| | 100 | 1000 | 0.70 | 1/10 |
| | 200 | 500 | 0.65 | 1/2.5 |
| | 200 | 600 | 0.70 | 1/3 |
| | 200 | 800 | 0.80 | 1/4 |
| | 200 | 1000 | 0.90 | 1/5 |
| | 300 | 400 | 0.80 | 1/1.3 |
| | 300 | 500 | 0.85 | 1/1.67 |
| | 300 | 600 | 0.90 | 1/2 |
| | 400 | 300 | 0.95 | 1/0.75 |
| | 500 | 0 | 1.00 | — |

The ratios of MIT to caprylic acid tested ranged from 1/0.027 to 1/2000. The synergistic ratios of MIT to caprylic acid range from 1/1.3 to 1/10. The MIT and caprylic acid combinations show enhanced control of mold.

TABLE 12

First Component (A) = Methylisothiazolinone (MIT)
Second Component (B) = Glycerol monolaurate

| Microorganism | $Q_a$ | $Q_b$ | SI | A/B |
|---|---|---|---|---|
| E. coli 8739 - M9GY (1 day) | 0 | 20000 | 1.00 | — |
| | 10 | 20000 | 1.33 | 1/2,000 |
| | 20 | 20000 | 1.67 | 1/1,000 |
| | 30.00 | 0 | 1.00 | — |
| C. albicans 10231 - PDB (6 days) | 0 | 20000 | 1.00 | — |
| | 50 | 20000 | 1.25 | 1/400 |
| | 100 | 20000 | 1.50 | 1/200 |
| | 200.00 | 0 | 1.00 | — |
| A. niger 16404 - PDB (10 days) | 0 | 20000 | 1.00 | — |
| | 200 | 20000 | 1.40 | 1/100 |
| | 400 | 800 | 0.84 | 1/2 |
| | 400 | 1000 | 0.85 | 1/2.5 |
| | 500.00 | 0 | 1.00 | — |

The ratios of MIT to glycerol monolaurate tested ranged from 1/0.027 to 1/2,000. The synergistic ratios of MIT to glycerol monolaurate range from 1/2 to 1/2.5. The MIT and glycerol monolaurate combinations show enhanced control of mold.

TABLE 13

First Component (A) = Methylisothiazolinone (MIT)
Second Component (B) = Glyceryl mono dicaprylate

| Microorganism | $Q_a$ | $Q_b$ | SI | A/B |
|---|---|---|---|---|
| E. coli 8739 - M9GY | 0 | 2000 | 1.00 | — |
| (1 day) | 5 | 2000 | 1.17 | 1/400 |
| | 10 | 2000 | 1.33 | 1/200 |
| | 15 | 2000 | 1.50 | 1/133 |
| | 20 | 2000 | 1.67 | 1/100 |
| | 30.00 | 0 | 1.00 | — |
| C. albicans 10231 - PDB | 0 | 100 | 1.00 | — |
| (2 days) | 25 | 60 | 0.77 | 1/2.4 |
| | 25 | 80 | 0.97 | 1/3.2 |
| | 50 | 40 | 0.73 | 1/0.8 |
| | 50 | 50 | 0.83 | 1/1 |
| | 50 | 60 | 0.93 | 1/1.2 |
| | 75 | 40 | 0.90 | 1/0.53 |
| | 150.00 | 0 | 1.00 | — |
| A. niger 16404 - PDB | 0 | 2000 | 1.00 | — |
| (10 days) | 100 | 2000 | 1.20 | 1/8,000 |
| | 200 | 2000 | 1.40 | 1/4,000 |
| | 400 | 2000 | 1.80 | 1/1,600 |
| | 500 | 0 | 1.00 | — |

The ratios of MIT to glyceryl mono dicaprylate tested ranged from 1/0.003 to 1/2000. The synergistic ratios of MIT to glyceryl mono dicaprylate range from 1/0.53 to 1/2.4. The MIT and glyceryl mono dicaprylate combinations show enhanced control of yeast.

TABLE 14

First Component (A) = Methylisothiazolinone (MIT)
Second Component (B) = Glyceryl caprate

| Microorganism | $Q_a$ | $Q_b$ | SI | A/B |
|---|---|---|---|---|
| E. coli 8739 - M9GY | 0 | 20000 | 1.00 | — |
| (1 day) | 5 | 20000 | 1.17 | 1/4,000 |
| | 10 | 20000 | 1.33 | 1/2,000 |
| | 15 | 20000 | 1.50 | 1/3,333 |
| | 20 | 20000 | 1.67 | 1/1,000 |
| | 30.00 | 0 | 1.00 | — |
| C. albicans 10231 - PDB | 0 | 2000 | 1.00 | — |
| (6 days) | 50 | 2000 | 1.25 | 1/40 |
| | 75 | 2000 | 1.38 | 1/27 |
| | 100 | 500 | 0.75 | 1/5 |
| | 100 | 600 | 0.80 | 1/6 |
| | 100 | 800 | 0.90 | 1/8 |
| | 150 | 30 | 0.77 | 1/0.2 |
| | 150 | 40 | 0.77 | 1/0.27 |
| | 150 | 50 | 0.78 | 1/0.33 |
| | 150 | 60 | 0.78 | 1/0.4 |
| | 150 | 80 | 0.79 | 1/0.53 |
| | 150 | 100 | 0.80 | 1/0.67 |
| | 150 | 200 | 0.85 | 1/1.33 |
| | 150 | 300 | 0.90 | 1/2 |
| | 150 | 400 | 0.95 | 1/2.7 |
| | 200.00 | 0 | 1.00 | — |
| A. niger 16404 - PDB | 0 | 2000 | 1.00 | — |
| (10 days) | 50 | 2000 | 1.10 | 1/40 |
| | 200 | 2000 | 1.40 | 1/10 |
| | 400 | 2000 | 1.80 | 1/5 |
| | 500 | 0 | 1.00 | — |

The ratios of MIT to glyceryl caprate tested ranged from 1/0.027 to 1/2,000. The synergistic ratios of MIT to glyceryl caprate range from 1/0.2 to 1/8. The MIT and glyceryl caprate combinations show enhanced control of yeast.

TABLE 15

First Component (A) = Methylisothiazolinone (MIT)
Second Component (B) = Propylene glycol caprylate

| Microorganism | $Q_a$ | $Q_b$ | SI | A/B |
|---|---|---|---|---|
| E. coli 8739 - M9GY | 0 | 20000 | 1.00 | — |
| (1 day) | 10 | 8000 | 0.73 | 1/800 |
| | 10 | 10000 | 0.83 | 1/1,000 |
| | 15 | 3000 | 0.65 | 1/200 |
| | 15 | 4000 | 0.70 | 1/267 |
| | 15 | 5000 | 0.75 | 1/333 |
| | 15 | 6000 | 0.80 | 1/400 |
| | 15 | 8000 | 0.90 | 1/533 |
| | 20 | 2000 | 0.77 | 1/100 |
| | 20 | 3000 | 0.82 | 1/150 |
| | 20 | 4000 | 0.87 | 1/200 |
| | 20 | 5000 | 0.92 | 1/250 |
| | 20 | 6000 | 0.97 | 1/300 |
| | 30.00 | 0 | 1.00 | — |
| C. albicans 10231 - PDB | 0 | 200 | 1.00 | — |
| (6 days) | 50 | 60 | 0.55 | 1/1.2 |
| | 50 | 80 | 0.65 | 1/1.6 |
| | 50 | 100 | 0.75 | 1/2 |
| | 75 | 50 | 0.63 | 1/0.67 |
| | 75 | 60 | 0.68 | 1/0.8 |
| | 75 | 80 | 0.78 | 1/1.07 |
| | 75 | 100 | 0.88 | 1/1.33 |
| | 100 | 30 | 0.65 | 1/0.30 |
| | 100 | 40 | 0.70 | 1/0.40 |
| | 100 | 50 | 0.75 | 1/0.50 |
| | 100 | 60 | 0.80 | 1/0.60 |
| | 100 | 80 | 0.90 | 1/0.80 |
| | 150 | 4 | 0.77 | 1/0.03 |
| | 150 | 6 | 0.78 | 1/0.04 |
| | 150 | 8 | 0.79 | 1/0.05 |
| | 150 | 10 | 0.80 | 1/0.07 |
| | 150 | 20 | 0.85 | 1/0.13 |
| | 150 | 30 | 0.90 | 1/0.20 |
| | 150 | 40 | 0.95 | 1/0.27 |
| | 200.00 | 0 | 1.00 | — |
| A. niger 16404 - PDB | 0 | 1000 | 1.00 | — |
| (3 days) | 50 | 600 | 0.73 | 1/12 |
| | 50 | 800 | 0.93 | 1/16 |
| | 100 | 600 | 0.85 | 1/6 |
| | 200 | 300 | 0.80 | 1/1.5 |
| | 200 | 400 | 0.90 | 1/2 |
| | 300 | 50 | 0.80 | 1/0.17 |
| | 300 | 60 | 0.81 | 1/0.2 |
| | 300 | 80 | 0.83 | 1/0.27 |
| | 300 | 100 | 0.85 | 1/0.33 |
| | 300 | 200 | 0.95 | 1/0.67 |
| | 400 | 0 | 1.00 | — |

The ratios of MIT to propylene glycol caprylate tested ranged from 1/0.003 to 1/2,000. The synergistic ratios of MIT to propylene glycol caprylate range from 1/0.03 to 1/1,000. The MIT and propylene glycol caprylate combinations show enhanced control of bacteria, yeast, and mold.

TABLE 16

First Component (A) = Methylisothiazolinone (MIT)
Second Component (B) = Propylene glycol monolaurate

| Microorganism | $Q_a$ | $Q_b$ | SI | A/B |
|---|---|---|---|---|
| E. coli 8739 - M9GY | 0 | 20000 | 1.00 | — |
| (1 day) | 10 | 20000 | 1.33 | 1/2,000 |
| | 15 | 20000 | 1.50 | 1/1,333 |
| | 20 | 20000 | 1.67 | 1/1,000 |
| | 30.00 | 0 | 1.00 | — |
| C. albicans 10231 - PDB | 0 | 20000 | 1.00 | — |
| (1 day) | 50 | 8000 | 0.90 | 1/160 |
| | 75 | 5000 | 1.00 | 1/67 |
| | 100.00 | 0 | 1.00 | — |

TABLE 16-continued

First Component (A) = Methylisothiazolinone (MIT)
Second Component (B) = Propylene glycol monolaurate

| Microorganism | $Q_a$ | $Q_b$ | SI | A/B |
|---|---|---|---|---|
| A. niger 16404 - PDB | 0 | 20000 | 1.00 | — |
| (10 days) | 400 | 4000 | 0.73 | 1/10 |
| | 400 | 5000 | 0.78 | 1/12.5 |
| | 400 | 6000 | 0.83 | 1/15 |
| | 400 | 8000 | 0.93 | 1/20 |
| | 500 | 2000 | 0.77 | 1/4 |
| | 500 | 3000 | 0.82 | 1/6 |
| | 500 | 4000 | 0.87 | 1/8 |
| | 500 | 5000 | 0.92 | 1/10 |
| | 500 | 6000 | 0.97 | 1/12 |
| | 750.00 | 0 | 1.00 | — |

The ratios of MIT to propylene glycol monolaurate tested ranged from 1/0.027 to 1/2,000. The synergistic ratios of MIT to propylene glycol monolaurate range from 1/4 to 1/20. The MIT and propylene glycol monolaurate combinations show enhanced control of yeast and mold.

TABLE 17

First Component (A) = Methylisothiazolinone (MIT)
Second Component (B) = Lauric arginate

| Microorganism | $Q_a$ | $Q_b$ | SI | A/B |
|---|---|---|---|---|
| E. coli 8739 - M9GY | 0 | 300 | 1.00 | — |
| (1 day) | 10 | 100 | 0.67 | 1/10 |
| | 15 | 100 | 0.83 | 1/6.7 |
| | 30.00 | 0 | 1.00 | — |
| C. albicans 10231 - PDB | 0 | 800 | 1.00 | — |
| (6 days) | 25 | 400 | 0.63 | 1/16 |
| | 25 | 500 | 0.75 | 1/20 |
| | 25 | 600 | 0.88 | 1/24 |
| | 50 | 300 | 0.63 | 1/6 |
| | 50 | 400 | 0.75 | 1/8 |
| | 50 | 500 | 0.88 | 1/10 |
| | 75 | 80 | 0.48 | 1/1 |
| | 75 | 100 | 0.50 | 1/1.33 |
| | 75 | 200 | 0.63 | 1/2.7 |
| | 75 | 300 | 0.75 | 1/4 |
| | 75 | 400 | 0.88 | 1/5.3 |
| | 100 | 30 | 0.54 | 1/0.3 |
| | 100 | 40 | 0.55 | 1/0.4 |
| | 100 | 50 | 0.56 | 1/0.5 |
| | 100 | 60 | 0.58 | 1/0.6 |
| | 100 | 80 | 0.60 | 1/0.8 |
| | 100 | 100 | 0.63 | 1/1 |
| | 100 | 200 | 0.75 | 1/2 |
| | 100 | 300 | 0.88 | 1/3 |
| | 150 | 4 | 0.76 | 1/0.03 |
| | 150 | 5 | 0.76 | 1/0.03 |
| | 150 | 6 | 0.76 | 1/0.04 |
| | 150 | 8 | 0.76 | 1/0.05 |
| | 150 | 10 | 0.76 | 1/0.07 |
| | 150 | 20 | 0.78 | 1/0.13 |
| | 150 | 30 | 0.79 | 1/0.20 |
| | 150 | 40 | 0.80 | 1/0.27 |
| | 150 | 50 | 0.81 | 1/0.33 |
| | 150 | 60 | 0.83 | 1/0.40 |
| | 150 | 80 | 0.85 | 1/0.53 |
| | 150 | 100 | 0.88 | 1/0.67 |
| | 200.00 | 0 | 1.00 | — |
| A. niger 16404 - PDB | 0 | 2000 | 1.00 | — |
| (10 days) | 50 | 800 | 0.47 | 1/16 |
| | 50 | 1000 | 0.57 | 1/20 |
| | 100 | 400 | 0.33 | 1/4 |
| | 100 | 500 | 0.38 | 1/5 |
| | 100 | 600 | 0.43 | 1/6 |
| | 100 | 800 | 0.53 | 1/8 |
| | 100 | 1000 | 0.63 | 1/10 |
| | 200 | 400 | 0.47 | 1/2 |
| | 200 | 500 | 0.52 | 1/2.5 |

TABLE 17-continued

First Component (A) = Methylisothiazolinone (MIT)
Second Component (B) = Lauric arginate

| Microorganism | $Q_a$ | $Q_b$ | SI | A/B |
|---|---|---|---|---|
| | 200 | 600 | 0.57 | 1/3 |
| | 200 | 800 | 0.67 | 1/4 |
| | 200 | 1000 | 0.77 | 1/5 |
| | 300 | 80 | 0.44 | 1/0.27 |
| | 300 | 100 | 0.45 | 1/0.33 |
| | 300 | 200 | 0.50 | 1/0.67 |
| | 300 | 300 | 0.55 | 1/1 |
| | 300 | 400 | 0.60 | 1/1.33 |
| | 300 | 500 | 0.65 | 1/1.67 |
| | 300 | 600 | 0.70 | 1.2 |
| | 300 | 800 | 0.80 | 1/2.67 |
| | 300 | 1000 | 0.90 | 1/3.33 |
| | 400 | 50 | 0.56 | 1/0.13 |
| | 400 | 60 | 0.56 | 1/0.15 |
| | 400 | 70 | 0.57 | 1/0.18 |
| | 400 | 80 | 0.57 | 1/0.20 |
| | 400 | 100 | 0.58 | 1/0.25 |
| | 400 | 200 | 0.63 | 1/0.5 |
| | 400 | 300 | 0.68 | 1/0.75 |
| | 400 | 400 | 0.73 | 1/1 |
| | 400 | 500 | 0.78 | 1/1.25 |
| | 400 | 600 | 0.83 | 1/1.5 |
| | 400 | 800 | 0.93 | 1/2 |
| | 500 | 30 | 0.68 | 1/0.06 |
| | 500 | 40 | 0.69 | 1/0.08 |
| | 500 | 50 | 0.69 | 1/0.10 |
| | 500 | 60 | 0.70 | 1/0.12 |
| | 500 | 80 | 0.71 | 1/0.16 |
| | 500 | 100 | 0.72 | 1/0.20 |
| | 500 | 200 | 0.77 | 1/0.40 |
| | 500 | 300 | 0.82 | 1/0.60 |
| | 500 | 400 | 0.87 | 1/0.80 |
| | 500 | 500 | 0.92 | 1/1 |
| | 500 | 600 | 0.97 | 1/1.2 |
| | 750 | 0 | 1.00 | — |

The ratios of MIT to lauric arginate tested ranged from 1/0.003 to 1/200. The synergistic ratios of MIT to lauric arginate range from 1/0.03 to 1/24. The MIT and lauric arginate combinations show enhanced control of bacteria, yeast, and mold.

TABLE 18

First Component (A) = Methylisothiazolinone (MIT)
Second Component (B) = Myristamidopropyl
PG-dimonium chloride phosphate

| Microorganism | $Q_a$ | $Q_b$ | SI | A/B |
|---|---|---|---|---|
| E. coli 8739 - M9GY | 0 | 80 | 1.00 | — |
| (1 day) | 10 | 50 | 0.96 | 1/5 |
| | 15 | 40 | 1.00 | 1/2.7 |
| | 20 | 30 | 1.04 | 1/1.5 |
| | 30.00 | 0 | 1.00 | — |
| C. albicans 10231 - PDB | 0 | 1000 | 1.00 | — |
| (6 days) | 25 | 500 | 0.63 | 1/20 |
| | 25 | 600 | 0.73 | 1/24 |
| | 25 | 800 | 0.93 | 1/32 |
| | 50 | 300 | 0.55 | 1/6 |
| | 50 | 400 | 0.65 | 1/8 |
| | 50 | 500 | 0.75 | 1/10 |
| | 50 | 600 | 0.85 | 1/12 |
| | 75 | 50 | 0.43 | 1/0.67 |
| | 75 | 60 | 0.44 | 1/0.8 |
| | 75 | 80 | 0.46 | 1/1.07 |
| | 75 | 100 | 0.48 | 1/1.33 |
| | 75 | 200 | 0.58 | 1/2.7 |
| | 75 | 300 | 0.68 | 1/4 |
| | 75 | 400 | 0.78 | 1/5.3 |
| | 75 | 500 | 0.88 | 1/6.7 |
| | 75 | 600 | 0.98 | 1/8 |

TABLE 18-continued

First Component (A) = Methylisothiazolinone (MIT)
Second Component (B) = Myristamidopropyl
PG-dimonium chloride phosphate

| Microorganism | $Q_a$ | $Q_b$ | SI | A/B |
|---|---|---|---|---|
| | 100 | 10 | 0.51 | 1/0.10 |
| | 100 | 20 | 0.52 | 1/0.2 |
| | 100 | 30 | 0.53 | 1/0.3 |
| | 100 | 40 | 0.54 | 1/0.4 |
| | 100 | 50 | 0.55 | 1/0.5 |
| | 100 | 60 | 0.56 | 1/0.6 |
| | 100 | 80 | 0.58 | 1/0.8 |
| | 100 | 100 | 0.60 | 1/1 |
| | 100 | 200 | 0.70 | 1/2 |
| | 100 | 300 | 0.80 | 1/3 |
| | 100 | 400 | 0.90 | 1/4 |
| | 150 | 2 | 0.75 | 1/0.01 |
| | 150 | 3 | 0.75 | 1/0.02 |
| | 150 | 4 | 0.75 | 1/0.03 |
| | 150 | 5 | 0.76 | 1/0.03 |
| | 150 | 6 | 0.76 | 1/0.04 |
| | 150 | 8 | 0.76 | 1/0.05 |
| | 150 | 10 | 0.76 | 1/0.07 |
| | 150 | 20 | 0.77 | 1/0.13 |
| | 150 | 30 | 0.78 | 1/0.20 |
| | 150 | 40 | 0.79 | 1/0.27 |
| | 150 | 50 | 0.80 | 1/0.33 |
| | 150 | 60 | 0.81 | 1/0.40 |
| | 150 | 80 | 0.83 | 1/0.53 |
| | 150 | 100 | 0.85 | 1/0.67 |
| | 150 | 200 | 0.95 | 1/1.33 |
| | 200.00 | 0 | 1.00 | — |
| *A. niger* 16404 - PDB (3 days) | 0 | 2000 | 1.00 | — |
| | 50 | 600 | 0.43 | 1/12 |
| | 50 | 800 | 0.53 | 1/16 |
| | 50 | 1000 | 0.63 | 1/20 |
| | 75 | 50 | 0.21 | 1/0.67 |
| | 75 | 100 | 0.24 | 1/1.33 |
| | 75 | 200 | 0.29 | 1/2.67 |
| | 75 | 300 | 0.34 | 1/4 |
| | 75 | 400 | 0.39 | 1/5.33 |
| | 75 | 500 | 0.44 | 1/6.67 |
| | 75 | 600 | 0.49 | 1/8 |
| | 75 | 800 | 0.59 | 1/11 |
| | 75 | 1000 | 0.69 | 1/13 |
| | 100 | 10 | 0.26 | 1/0.10 |
| | 100 | 20 | 0.26 | 1/0.20 |
| | 100 | 30 | 0.27 | 1/0.30 |
| | 100 | 40 | 0.27 | 1/0.40 |
| | 100 | 50 | 0.28 | 1/0.50 |
| | 100 | 60 | 0.28 | 1/0.60 |
| | 100 | 80 | 0.29 | 1/0.80 |
| | 100 | 100 | 0.30 | 1/1 |
| | 100 | 200 | 0.35 | 1/2 |
| | 100 | 300 | 0.40 | 1/3 |
| | 100 | 400 | 0.45 | 1/4 |
| | 100 | 500 | 0.50 | 1/5 |
| | 100 | 600 | 0.55 | 1/6 |
| | 100 | 800 | 0.65 | 1/8 |
| | 100 | 1000 | 0.75 | 1/10 |
| | 150 | 2 | 0.38 | 1/0.01 |
| | 150 | 3 | 0.38 | 1/0.02 |
| | 150 | 4 | 0.38 | 1/0.03 |
| | 150 | 5 | 0.38 | 1/0.03 |
| | 150 | 6 | 0.38 | 1/0.04 |
| | 150 | 8 | 0.38 | 1.0.05 |
| | 150 | 10 | 0.38 | 1/0.07 |
| | 150 | 20 | 0.39 | 1/0.13 |
| | 150 | 30 | 0.39 | 1.0.20 |
| | 150 | 40 | 0.40 | 1/0.27 |
| | 150 | 50 | 0.40 | 1/0.33 |
| | 150 | 60 | 0.41 | 1/0.40 |
| | 150 | 80 | 0.42 | 1/0.53 |
| | 150 | 100 | 0.43 | 1/0.67 |
| | 150 | 200 | 0.48 | 0/1.33 |
| | 150 | 300 | 0.53 | 1/2 |
| | 150 | 400 | 0.58 | 1/2.67 |
| | 150 | 500 | 0.63 | 1/3.33 |
| | 150 | 600 | 0.68 | 1/4 |
| | 150 | 800 | 0.78 | 1/5.33 |
| | 150 | 1000 | 0.88 | 1/6.67 |
| | 400 | 0 | 1.00 | — |

The ratios of MIT to myristamidopropyl PG-dimonium chloride phosphate tested ranged from 1/0.0003 to 1/200. The synergistic ratios of MIT to myristamidopropyl PG-dimonium chloride phosphate range from 1/0.01 to 1/32. The MIT and myristamidopropyl PG-dimonium chloride phosphate combinations show enhanced control of yeast and mold.

TABLE 19

First Component (A) = Methylisothiazolinone (MIT)
Second Component (B) = Ethylhexylglycerin

| Microorganism | $Q_a$ | $Q_b$ | SI | A/B |
|---|---|---|---|---|
| *E. coli* 8739 - M9GY (6 days) | 0 | 3000 | 1.00 | — |
| | 5 | 2000 | 0.79 | 1/400 |
| | 10 | 2000 | 0.92 | 1/200 |
| | 20 | 2000 | 1.17 | 1/100 |
| | 40.00 | 0 | 1.00 | — |
| *C. albicans* 10231 - PDB (6 days) | 0 | 2000 | 1.00 | — |
| | 50 | 2000 | 1.25 | 1/40 |
| | 100 | 2000 | 1.50 | 1/20 |
| | 150 | 200 | 0.85 | 1/1.33 |
| | 150 | 300 | 0.90 | 1/2 |
| | 150 | 400 | 0.95 | 1/2.7 |
| | 200.00 | 0 | 1.00 | — |
| *A. niger* 16404 - PDB (10 days) | 0 | 2000 | 1.00 | — |
| | 400 | 800 | 0.93 | 1/2 |
| | 500 | 300 | 0.82 | 1/0.6 |
| | 500 | 400 | 0.87 | 1/0.8 |
| | 500 | 500 | 0.92 | 1/1 |
| | 500 | 600 | 0.97 | 1/1.2 |
| | 750 | 0 | 1.00 | — |

The ratios of MIT to ethylhexylglycerin tested ranged from 1/0.027 to 1/2,000. The synergistic ratios of MIT to ethylhexylglycerin range from 1/0.6 to 1/400. The MIT and ethylhexylglycerin combinations show enhanced control of bacteria, yeast, and mold.

TABLE 20

First Component (A) = Benzisothiazolinone (BIT)
Second Component (B) = Caprylic acid

| Microorganism | $Q_a$ | $Q_b$ | SI | A/B |
|---|---|---|---|---|
| *E. coli* 8739 - M9GY (1 day) | 0 | 8000 | 1.00 | — |
| | 2.5 | 6000 | 0.88 | 1/2400 |
| | 5 | 3000 | 0.63 | 1/600 |
| | 5 | 4000 | 0.75 | 1/800 |
| | 5 | 5000 | 0.88 | 1/1,000 |
| | 7.5 | 3000 | 0.75 | 1/400 |
| | 7.5 | 4000 | 0.88 | 1/533 |
| | 10 | 2000 | 0.75 | 1/200 |
| | 10 | 3000 | 0.88 | 1/300 |
| | 20 | 0 | 1.00 | — |
| *C. albicans* 10231 - PDB (6 days) | 0 | 2000 | 1.00 | — |
| | 5 | 2000 | 1.25 | 1/400 |
| | 10 | 2000 | 1.50 | 1/200 |
| | 15 | 2000 | 1.75 | 1/133 |
| | 20 | 0 | 1.00 | — |

TABLE 20-continued

First Component (A) = Benzisothiazolinone (BIT)
Second Component (B) = Caprylic acid

| Microorganism | $Q_a$ | $Q_b$ | SI | A/B |
|---|---|---|---|---|
| A. niger 16404 - PDB (3 days) | 0 | 2000 | 1.00 | — |
| | 15 | 2000 | 1.30 | 1/133 |
| | 25 | 200 | 0.60 | 1/8 |
| | 25 | 300 | 0.65 | 1/12 |
| | 25 | 400 | 0.70 | 1/16 |
| | 25 | 500 | 0.75 | 1/20 |
| | 25 | 600 | 0.80 | 1/24 |
| | 25 | 800 | 0.90 | 1/32 |
| | 50 | 0 | 1.00 | — |

The ratios of BIT to caprylic acid tested ranged from 1/0.10 to 1/10,000. The synergistic ratios of BIT to caprylic acid range from 1/8 to 1/2,400. The BIT and caprylic acid combinations show enhanced control of bacteria and mold.

TABLE 21

First Component (A) = Benzisothiazolinone (BIT)
Second Component (B) = Glycerol monolaurate

| Microorganism | $Q_a$ | $Q_b$ | SI | A/B |
|---|---|---|---|---|
| E. coli 8739 - M9GY (1 day) | 0 | 20000 | 1.00 | — |
| | 5 | 20000 | 1.25 | 1/4,000 |
| | 10 | 20000 | 1.50 | 1/2,000 |
| | 20.00 | 0 | 1.00 | — |
| C. albicans 10231 - PDB (6 days) | 0 | 20000 | 1.00 | — |
| | 15 | 600 | 0.53 | 1/40 |
| | 15 | 800 | 0.54 | 1/53 |
| | 15 | 1000 | 0.55 | 1/67 |
| | 15 | 2000 | 0.60 | 1/133 |
| | 15 | 3000 | 0.65 | 1/200 |
| | 15 | 4000 | 0.70 | 1/267 |
| | 15 | 5000 | 0.75 | 1/333 |
| | 15 | 6000 | 0.80 | 1/400 |
| | 15 | 8000 | 0.90 | 1/533 |
| | 20 | 200 | 0.68 | 1/10 |
| | 20 | 300 | 0.68 | 1/15 |
| | 20 | 400 | 0.69 | 1/20 |
| | 20 | 500 | 0.69 | 1/25 |
| | 20 | 600 | 0.70 | 1/30 |
| | 20 | 800 | 0.71 | 1/40 |
| | 20 | 1000 | 0.72 | 1/50 |
| | 20 | 2000 | 0.77 | 1/100 |
| | 20 | 3000 | 0.82 | 1/150 |
| | 20 | 4000 | 0.87 | 1/200 |
| | 20 | 5000 | 0.92 | 1/250 |
| | 20 | 6000 | 0.97 | 1/300 |
| | 30.00 | 0 | 1.00 | — |
| A. niger 16404 - PDB (10 days) | 0 | 20000 | 1.00 | — |
| | 25 | 4000 | 0.45 | 1/160 |
| | 25 | 5000 | 0.50 | 1/200 |
| | 25 | 6000 | 0.55 | 1/240 |
| | 25 | 8000 | 0.65 | 1/320 |
| | 25 | 10000 | 0.75 | 1/400 |
| | 50 | 500 | 0.53 | 1/10 |
| | 50 | 600 | 0.53 | 1/12 |
| | 50 | 800 | 0.54 | 1/16 |
| | 50 | 1000 | 0.55 | 1/20 |
| | 50 | 2000 | 0.60 | 1/40 |
| | 50 | 3000 | 0.65 | 1/60 |
| | 50 | 4000 | 0.70 | 1/80 |
| | 50 | 5000 | 0.75 | 1/100 |
| | 50 | 6000 | 0.80 | 1/120 |
| | 50 | 8000 | 0.90 | 1/160 |
| | 100.00 | 0 | 1.00 | — |

The ratios of BIT to glycerol monolaurate tested ranged from 1/0.10 to 1/10,000. The synergistic ratios of BIT to glycerol monolaurate range from 1/10 to 1/533. The BIT and glycerol monolaurate combinations show enhanced control of yeast and mold.

TABLE 22

First Component (A) = Benzisothiazolinone (BIT)
Second Component (B) = Glyceryl mono dicaprylate

| Microorganism | $Q_a$ | $Q_b$ | SI | A/B |
|---|---|---|---|---|
| E. coli 8739 - M9GY (1 day) | 0 | 3000 | 1.00 | — |
| | 2.5 | 3000 | 1.13 | 1/1200 |
| | 5 | 2000 | 0.92 | 1/400 |
| | 7.5 | 2000 | 1.04 | 1/267 |
| | 10 | 2000 | 1.17 | 1/200 |
| | 20.00 | 0 | 1.00 | — |
| C. albicans 10231 - PDB (1 day) | 0 | 80 | 1.00 | — |
| | 2.5 | 60 | 0.92 | 1/24 |
| | 5 | 40 | 0.83 | 1/8 |
| | 5 | 50 | 0.96 | 1/10 |
| | 5 | 60 | 1.08 | 1/12 |
| | 10 | 30 | 1.04 | 1/3 |
| | 15.00 | 0 | 1.00 | — |
| A. niger 16404 - PDB (3 days) | 0 | 2000 | 1.00 | — |
| | 5 | 2000 | 1.10 | 1/8,000 |
| | 10 | 2000 | 1.20 | 1/4,000 |
| | 15 | 2000 | 1.30 | 1/1,600 |
| | 25 | 2000 | 1.50 | 1/2,000 |
| | 50 | 0 | 1.00 | — |

The ratios of BIT to Glyceryl mono dicaprylate tested ranged from 1/0.01 to 1/10,000. The synergistic ratios of BIT to Glyceryl mono dicaprylate range from 1/8 to 1/400. The BIT and Glyceryl mono dicaprylate combinations show enhanced control of bacteria and yeast.

TABLE 23

First Component (A) = Benzisothiazolinone (BIT)
Second Component (B) = Glyceryl caprate

| Microorganism | $Q_a$ | $Q_b$ | SI | A/B |
|---|---|---|---|---|
| E. coli 8739 - M9GY (1 day) | 0 | 20000 | 1.00 | — |
| | 2.5 | 20000 | 1.13 | 1/8,000 |
| | 5 | 20000 | 1.25 | 1/4,000 |
| | 7.5 | 20000 | 1.38 | 1/2,667 |
| | 10 | 20000 | 1.50 | 1/2,000 |
| | 20.00 | 0 | 1.00 | — |
| C. albicans 10231 - PDB (6 days) | 0 | 2000 | 1.00 | — |
| | 15 | 800 | 0.78 | 1/53 |
| | 15 | 1000 | 0.88 | 1/67 |
| | 20 | 300 | 0.65 | 1/15 |
| | 20 | 400 | 0.70 | 1/20 |
| | 20 | 500 | 0.75 | 1/25 |
| | 20 | 600 | 0.80 | 1/30 |
| | 20 | 800 | 0.90 | 1/40 |
| | 30 | 30 | 0.77 | 1/1 |
| | 30 | 40 | 0.77 | 1/1.3 |
| | 30 | 50 | 0.78 | 1/1.67 |
| | 30 | 60 | 0.78 | 1/2 |
| | 30 | 80 | 0.79 | 1/2.67 |
| | 30 | 100 | 0.80 | 1/3.33 |
| | 30 | 200 | 0.85 | 1/6.67 |
| | 30 | 300 | 0.90 | 1/10 |
| | 30 | 400 | 0.95 | 1/13 |
| | 40.00 | 0 | 1.00 | — |
| A. niger 16404 - PDB (3 days) | 0 | 2000 | 1.00 | — |
| | 25 | 800 | 0.90 | 1/32 |
| | 50 | 0 | 1.00 | — |

The ratios of BIT to glyceryl caprate tested ranged from 1/0.10 to 1/10,000. The synergistic ratios of BIT to glyceryl caprate range from 1/1 to 1/67. The BIT and glyceryl caprate combinations show enhanced control of yeast and mold.

TABLE 24

First Component (A) = Benzisothiazolinone (BIT)
Second Component (B) = Propylene glycol caprylate

| Microorganism | $Q_a$ | $Q_b$ | SI | A/B |
|---|---|---|---|---|
| E. coli 8739 - M9GY | 0 | 20000 | 1.00 | — |
| (1 day) | 5 | 6000 | 0.55 | 1/1,200 |
|  | 5 | 8000 | 0.65 | 1/1,600 |
|  | 5 | 10000 | 0.75 | 1/2,000 |
|  | 7.5 | 3000 | 0.53 | 1/400 |
|  | 7.5 | 4000 | 0.58 | 1/533 |
|  | 7.5 | 5000 | 0.63 | 1/667 |
|  | 7.5 | 6000 | 0.68 | 1/800 |
|  | 7.5 | 8000 | 0.78 | 1/1,067 |
|  | 7.5 | 10000 | 0.88 | 1/1,333 |
|  | 10 | 2000 | 0.60 | 1/200 |
|  | 10 | 3000 | 0.65 | 1/300 |
|  | 10 | 4000 | 0.70 | 1/400 |
|  | 10 | 5000 | 0.75 | 1/500 |
|  | 10 | 6000 | 0.80 | 1/600 |
|  | 10 | 8000 | 0.90 | 1/800 |
|  | 20.00 | 0 | 1.00 | — |
| C. albicans 10231 - PDB | 0 | 80 | 1.00 | — |
| (2 days) | 2.5 | 50 | 0.71 | 1/20 |
|  | 2.5 | 60 | 0.83 | 1/24 |
|  | 5 | 50 | 0.79 | 1/10 |
|  | 5 | 60 | 0.92 | 1/12 |
|  | 15 | 30 | 0.88 | 1/2 |
|  | 20 | 4 | 0.72 | 1/0.20 |
|  | 20 | 5 | 0.73 | 1/0.25 |
|  | 20 | 6 | 0.74 | 1/0.30 |
|  | 20 | 8 | 0.77 | 1/0.40 |
|  | 20 | 10 | 0.79 | 1/0.50 |
|  | 20 | 20 | 0.92 | 1/1 |
|  | 30.00 | 0 | 1.00 | — |
| A. niger 16404 - PDB | 0 | 1000 | 1.00 | — |
| (3 days) | 10 | 500 | 0.70 | 1/50 |
|  | 10 | 600 | 0.80 | 1/60 |
|  | 15 | 300 | 0.60 | 1/20 |
|  | 15 | 400 | 0.70 | 1/27 |
|  | 15 | 500 | 0.80 | 1/33 |
|  | 15 | 600 | 0.90 | 1/40 |
|  | 25 | 80 | 0.58 | 1/3.2 |
|  | 25 | 100 | 0.60 | 1/4 |
|  | 25 | 200 | 0.70 | 1/8 |
|  | 25 | 300 | 0.80 | 1/12 |
|  | 25 | 400 | 0.90 | 1/16 |
|  | 50 | 0 | 1.00 | — |

The ratios of BIT to propylene glycol caprylate tested ranged from 1/0.01 to 1/10,000. The synergistic ratios of BIT to propylene glycol caprylate range from 1/0.20 to 1/2,000. The BIT and propylene glycol caprylate combinations show enhanced control of bacteria, yeast, and mold.

TABLE 25

First Component (A) = Benzisothiazolinone (BIT)
Second Component (B) = Propylene glycol monolaurate

| Microorganism | $Q_a$ | $Q_b$ | SI | A/B |
|---|---|---|---|---|
| E. coli 8739 - M9GY | 0 | 20000 | 1.00 | — |
| (1 day) | 2.5 | 20000 | 1.13 | 1/8,000 |
|  | 5 | 20000 | 1.25 | 1/4,000 |
|  | 7.5 | 20000 | 1.38 | 1/2,667 |
|  | 10 | 20000 | 1.50 | 1/2,000 |
|  | 20.00 | 0 | 1.00 | — |
| C. albicans 10231 - PDB | 0 | 10000 | 1.00 | — |
| (6 days) | 2.5 | 6000 | 0.68 | 1/2,400 |
|  | 2.5 | 8000 | 0.88 | 1/3,200 |
|  | 5 | 5000 | 0.67 | 1/1,000 |
|  | 5 | 6000 | 0.77 | 1/1,200 |
|  | 5 | 8000 | 0.97 | 1/1,600 |
|  | 10 | 3000 | 0.63 | 1/300 |
|  | 10 | 4000 | 0.73 | 1/400 |
|  | 10 | 5000 | 0.83 | 1/500 |
|  | 10 | 6000 | 0.93 | 1/600 |
|  | 30.00 | 0 | 1.00 | — |
| A. niger 16404 - PDB | 0 | 20000 | 1.00 | — |
| (3 days) | 5 | 20000 | 1.10 | 1/4,000 |
|  | 10 | 20000 | 1.20 | 1/2,000 |
|  | 15 | 20000 | 1.30 | 1/1,333 |
|  | 25 | 20000 | 1.50 | 1/800 |
|  | 50 | 0 | 1.00 | — |

The ratios of BIT to propylene glycol monolaurate tested ranged from 1/0.1 to 1/10,000. The synergistic ratios of BIT to propylene glycol monolaurate range from 1/300 to 1/3,200. The BIT and propylene glycol monolaurate combinations show enhanced control of yeast.

TABLE 26

First Component (A) = Benzisothiazolinone (BIT)
Second Component (B) = Lauric arginate

| Microorganism | $Q_a$ | $Q_b$ | SI | A/B |
|---|---|---|---|---|
| E. coli 8739 - M9GY | 0 | 300 | 1.00 | — |
| (1 day) | 2.5 | 300 | 1.13 | 1/120 |
|  | 5 | 300 | 1.25 | 1/60 |
|  | 7.5 | 200 | 1.04 | 1/27 |
|  | 10 | 200 | 1.17 | 1/20 |
|  | 20.00 | 0 | 1.00 | — |
| C. albicans 10231 - PDB | 0 | 200 | 1.00 | — |
| (6 days) | 15 | 80 | 0.78 | 1/5.33 |
|  | 15 | 100 | 0.88 | 1/6.67 |
|  | 20 | 30 | 0.65 | 1/1.5 |
|  | 20 | 40 | 0.70 | 1/2 |
|  | 20 | 50 | 0.75 | 1/2.5 |
|  | 20 | 60 | 0.80 | 1/3 |
|  | 20 | 80 | 0.90 | 1/4 |
|  | 30 | 3 | 0.77 | 1/0.10 |
|  | 30 | 4 | 0.77 | 1/0.13 |
|  | 30 | 5 | 0.78 | 1/0.17 |
|  | 30 | 6 | 0.78 | 1/0.20 |
|  | 30 | 8 | 0.79 | 1/0.27 |
|  | 30 | 10 | 0.80 | 1/0.33 |
|  | 30 | 20 | 0.85 | 1/0.67 |
|  | 30 | 30 | 0.90 | 1/1 |
|  | 30 | 40 | 0.95 | 1/1.33 |
|  | 40.00 | 0 | 1.00 | — |
| A. niger 16404 - PDB | 0 | 2000 | 1.00 | — |
| (3 days) | 5 | 600 | 0.40 | 1/120 |
|  | 5 | 800 | 0.50 | 1/160 |
|  | 5 | 1000 | 0.60 | 1/200 |
|  | 10 | 400 | 0.40 | 1/40 |
|  | 10 | 500 | 0.45 | 1/50 |
|  | 10 | 600 | 0.50 | 1/60 |
|  | 10 | 800 | 0.60 | 1/80 |
|  | 10 | 1000 | 0.70 | 1/100 |
|  | 15 | 200 | 0.40 | 1/13 |
|  | 15 | 300 | 0.45 | 1/20 |
|  | 15 | 400 | 0.50 | 1/27 |
|  | 15 | 500 | 0.55 | 1/33 |
|  | 15 | 600 | 0.60 | 1/40 |
|  | 15 | 800 | 0.70 | 1/53 |
|  | 15 | 1000 | 0.80 | 1/67 |
|  | 25 | 20 | 0.51 | 1/0.80 |
|  | 25 | 30 | 0.52 | 1/1.20 |
|  | 25 | 40 | 0.52 | 1/1.60 |
|  | 25 | 50 | 0.53 | 1/2 |
|  | 25 | 60 | 0.53 | 1/2.4 |
|  | 25 | 80 | 0.54 | 1/3.2 |
|  | 25 | 100 | 0.55 | 1/4 |
|  | 25 | 200 | 0.60 | 1/8 |
|  | 25 | 300 | 0.65 | 1/12 |

TABLE 26-continued

| First Component (A) = Benzisothiazolinone (BIT) Second Component (B) = Lauric arginate | | | | |
|---|---|---|---|---|
| Microorganism | $Q_a$ | $Q_b$ | SI | A/B |
| | 25 | 400 | 0.70 | 1/16 |
| | 25 | 500 | 0.75 | 1/20 |
| | 25 | 600 | 0.80 | 1/24 |
| | 25 | 800 | 0.90 | 1/32 |
| | 50 | 0 | 1.00 | — |

The ratios of BIT to lauric arginate tested ranged from 1/0.010 to 1/1,000. The synergistic ratios of BIT to lauric arginate range from 1/0.1 to 1/200. The BIT and lauric arginate combinations show enhanced control of yeast and mold.

TABLE 27

| First Component (A) = Benzisothiazolinone (BIT) Second Component (B) = Myristamidopropyl PG-dimonium chloride phosphate | | | | |
|---|---|---|---|---|
| Microorganism | $Q_a$ | $Q_b$ | SI | A/B |
| E. coli 8739 - M9GY (1 day) | 0 | 80 | 1.00 | — |
| | 1 | 60 | 0.80 | 1/60 |
| | 2.5 | 50 | 0.75 | 1/20 |
| | 2.5 | 60 | 0.88 | 1/24 |
| | 10 | 30 | 0.88 | 1/3 |
| | 20.00 | 0 | 1.00 | — |
| C. albicans 10231 - PDB (2 days) | 0 | 2000 | 1.00 | — |
| | 10 | 1000 | 0.83 | 1/100 |
| | 15 | 10 | 0.51 | 1/0.67 |
| | 15 | 20 | 0.51 | 1/1.33 |
| | 15 | 30 | 0.52 | 1/2 |
| | 15 | 40 | 0.52 | 1/2.67 |
| | 15 | 50 | 0.53 | 1/3.33 |
| | 15 | 60 | 0.53 | 1/4 |
| | 15 | 80 | 0.54 | 1/5.33 |
| | 15 | 100 | 0.55 | 1/6.67 |
| | 15 | 200 | 0.60 | 1/13.3 |
| | 15 | 300 | 0.65 | 1/20 |
| | 15 | 400 | 0.70 | 1/27 |
| | 15 | 500 | 0.75 | 1/33 |
| | 15 | 600 | 0.80 | 1/40 |
| | 15 | 800 | 0.90 | 1/53 |
| | 20 | 4 | 0.67 | 1/0.20 |
| | 20 | 5 | 0.67 | 1/0.25 |
| | 20 | 6 | 0.67 | 1/0.30 |
| | 20 | 8 | 0.67 | 1/0.40 |
| | 20 | 10 | 0.67 | 1/0.50 |
| | 20 | 20 | 0.68 | 1/1 |
| | 20 | 30 | 0.68 | 1/1.5 |
| | 20 | 40 | 0.69 | 1/2 |
| | 20 | 50 | 0.69 | 1/2.5 |
| | 20 | 60 | 0.70 | 1/3 |
| | 20 | 80 | 0.71 | 1/4 |
| | 20 | 100 | 0.72 | 1/5 |
| | 20 | 200 | 0.77 | 1/10 |
| | 20 | 300 | 0.82 | 1/15 |
| | 20 | 400 | 0.87 | 1/20 |
| | 20 | 500 | 0.92 | 1/25 |
| | 20 | 600 | 0.97 | 1/30 |
| | 30.00 | 0 | 1.00 | — |
| A. niger 16404 - PDB (4 days) | 0 | 2000 | 1.00 | — |
| | 5 | 800 | 0.50 | 1/160 |
| | 5 | 1000 | 0.60 | 1/200 |
| | 10 | 800 | 0.60 | 1/80 |
| | 10 | 1000 | 0.70 | 1/100 |
| | 15 | 400 | 0.50 | 1/27 |
| | 15 | 600 | 0.60 | 1/40 |
| | 15 | 800 | 0.70 | 1/53 |
| | 15 | 1000 | 0.80 | 1/67 |
| | 25 | 600 | 0.80 | 1/24 |
| | 25 | 800 | 0.90 | 1/32 |
| | 50 | 0 | 1.00 | — |

The ratios of BIT to myristamidopropyl PG-dimonium chloride phosphate tested ranged from 1/0.001 to 1/1,000. The synergistic ratios of BIT to myristamidopropyl PG-dimonium chloride phosphate range from 1/0.2 to 1/200. The BIT and myristamidopropyl PG-dimonium chloride phosphate combinations show enhanced control of bacteria, yeast, and mold.

TABLE 28

| First Component (A) = Bnzisothiazolinone (BIT) Second Component (B) = Ehylhexylglycerin | | | | |
|---|---|---|---|---|
| Microorganism | $Q_a$ | $Q_b$ | SI | A/B |
| E. coli 8739 - M9GY (2 days) | 0 | 3000 | 1.00 | — |
| | 2.5 | 3000 | 1.13 | 1/200 |
| | 5 | 2000 | 0.92 | 1/400 |
| | 7.2 | 2000 | 1.03 | 1/278 |
| | 10 | 2000 | 1.17 | 1/200 |
| | 20.00 | 0 | 1.00 | — |
| C. albicans 10231 - PDB (6 days) | 0 | 10000 | 1.00 | — |
| | 2.5 | 5000 | 0.58 | 1/2,000 |
| | 2.5 | 6000 | 0.68 | 1/2,400 |
| | 2.5 | 8000 | 0.88 | 1/3,200 |
| | 5 | 4000 | 0.57 | 1/800 |
| | 5 | 5000 | 0.67 | 1/1,000 |
| | 5 | 6000 | 0.77 | 1/1,200 |
| | 5 | 8000 | 0.97 | 1/1,600 |
| | 10 | 3000 | 0.63 | 1/300 |
| | 10 | 4000 | 0.73 | 1/400 |
| | 10 | 5000 | 0.83 | 1/500 |
| | 10 | 6000 | 0.93 | 1/600 |
| | 15 | 300 | 0.53 | 1/20 |
| | 15 | 400 | 0.54 | 1/27 |
| | 15 | 500 | 0.55 | 1/33 |
| | 15 | 600 | 0.56 | 1/40 |
| | 15 | 800 | 0.58 | 1/53 |
| | 15 | 1000 | 0.60 | 1/67 |
| | 15 | 2000 | 0.70 | 1/133 |
| | 15 | 3000 | 0.80 | 1/200 |
| | 15 | 4000 | 0.90 | 1/267 |
| | 20 | 30 | 0.67 | 1/1.5 |
| | 20 | 40 | 0.67 | 1/2 |
| | 20 | 50 | 0.67 | 1/2.5 |
| | 20 | 60 | 0.67 | 1/3 |
| | 20 | 80 | 0.67 | 1/4 |
| | 20 | 100 | 0.68 | 1/5 |
| | 20 | 200 | 0.69 | 1/10 |
| | 20 | 300 | 0.70 | 1/15 |
| | 20 | 400 | 0.71 | 1/20 |
| | 20 | 500 | 0.72 | 1/25 |
| | 20 | 600 | 0.73 | 1/30 |
| | 20 | 800 | 0.75 | 1/40 |
| | 20 | 1000 | 0.77 | 1/50 |
| | 20 | 2000 | 0.87 | 1/100 |
| | 20 | 3000 | 0.97 | 1/150 |
| | 30.00 | 0 | 1.00 | — |
| A. niger 16404 - PDB (3 days) | 0 | 2000 | 1.00 | — |
| | 5 | 2000 | 1.10 | 1/400 |
| | 10 | 2000 | 1.20 | 1/200 |
| | 15 | 2000 | 1.30 | 1/133 |
| | 25 | 2000 | 1.50 | 1/80 |
| | 50 | 0 | 1.00 | — |

The ratios of BIT to ethylhexylglycerin tested ranged from 1/0.1 to 1/10,000. The synergistic ratios of BIT to ethylhexylglycerin range from 1/1.5 to 1/3,200. The BIT and ethylhexylglycerin combinations show enhanced control of bacteria and yeast.

We claim:
1. A composition comprising a synergistic mixture of:
   (a) 1,2-benzisothiazolin-3-one; and
   (b) one or more compounds selected from the group consisting of caprylic acid, glycerol monolaurate, glyceryl mono dicaprylate, glyceryl caprylate, propylene glycol caprylate, propylene glycol monolaurate, and lauric arginate.

* * * * *